(12) United States Patent
Li et al.

(10) Patent No.: US 11,206,846 B2
(45) Date of Patent: Dec. 28, 2021

(54) HIGH PURITY ALPHA LACTALBUMIN AND METHODS OF MAKING

(71) Applicant: Leprino Foods Company, Denver, CO (US)

(72) Inventors: Jiancai Li, Englewood, CO (US); Richard K. Merrill, Highlands Ranch, CO (US); Ranjeeta Wadhwani, Westminster, CO (US)

(73) Assignee: Leprino Foods Company, Denver, CO (US)

( * ) Notice: Subject to any disclaimer, the term of this patent is extended or adjusted under 35 U.S.C. 154(b) by 477 days.

(21) Appl. No.: 15/947,289

(22) Filed: Apr. 6, 2018

(65) Prior Publication Data
US 2018/0317513 A1 Nov. 8, 2018

Related U.S. Application Data

(60) Provisional application No. 62/500,354, filed on May 2, 2017.

(51) Int. Cl.
*A23C 21/06* (2006.01)
*C07K 14/76* (2006.01)
(Continued)

(52) U.S. Cl.
CPC ............ *A23C 21/06* (2013.01); *A23C 9/1422* (2013.01); *A23C 21/02* (2013.01); *A23C 21/10* (2013.01);
(Continued)

(58) Field of Classification Search
CPC .......... A23C 21/06; A23C 21/02; A23C 21/10
See application file for complete search history.

(56) References Cited

U.S. PATENT DOCUMENTS 4,528,203 A * 7/1985 Harris .................... A23J 1/205
426/555
5,008,376 A    4/1991 Bottomley
(Continued)

OTHER PUBLICATIONS

Cheison, et al., "Influence of hydrolysis temperature and pH on the selective hydrolysis of whey proteins by trypsin and potential recovery of native alpha-lactoglobulin", International Dairy Journal, vol. 21 Issue 3, Mar. 2011, pp. 166-171.
PCT/US2018/030211 received an International Search Report and Written Opinion dated Jul. 19, 2018, 11 pages.

*Primary Examiner* — Felicia C Turner
(74) *Attorney, Agent, or Firm* — Kilpatrick Townsend & Stockton, LLP

(57) ABSTRACT

Methods and systems for making a high-purity α-lactalbumin composition are described. The composition may be made by providing a whey protein mixture, and adding an alkaline solution to the mixture to make the mixture alkaline and promote the aggregation of ß-lactoglobulin proteins. The alkaline whey protein mixture is filtered into a ß-LG aggregate composition and a α-LA enriched composition. A final α-lactalbumin enriched composition sourced from the α-LA enriched composition is dried into the high-purity α-lactalbumin composition (a powdered dairy composition) that is at least 70 wt. % α-lactalbumin on a protein basis. A protease enzyme may optionally be added to the α-LA enriched composition to form an enzymatically treated α-LA enriched composition that becomes the source of the final α-lactalbumin enriched composition.

28 Claims, 6 Drawing Sheets

(51) Int. Cl.
*A23J 3/08* (2006.01)
*A23C 21/02* (2006.01)
*A23C 9/142* (2006.01)
*A23L 19/12* (2016.01)
*A23J 1/20* (2006.01)
*A23J 3/34* (2006.01)
*A23L 33/19* (2016.01)
*A23C 21/10* (2006.01)

(52) U.S. Cl.
CPC ........... *A23J 1/205* (2013.01); *A23J 3/08* (2013.01); *A23J 3/34* (2013.01); *A23L 19/14* (2016.08); *A23L 33/19* (2016.08); *C07K 14/76* (2013.01); *A23C 2220/106* (2013.01)

(56) References Cited

U.S. PATENT DOCUMENTS

| | | |
|---|---|---|
| 5,322,773 A | 6/1994 | Kaneko et al. |
| 5,420,249 A * | 5/1995 | de Wit ............... A23C 9/146 530/365 |
| 5,455,331 A | 10/1995 | Pearce |
| 5,503,864 A | 4/1996 | Uchida et al. |
| 5,700,904 A | 12/1997 | Baker et al. |
| 5,986,063 A | 11/1999 | Etzel |
| 6,139,901 A | 10/2000 | Blazey et al. |
| 6,613,377 B2 | 9/2003 | Wu |
| 7,585,537 B2 | 9/2009 | Merrill et al. |
| 8,101,377 B2 | 1/2012 | Blanton et al. |
| 2009/0028990 A1 | 1/2009 | Kwon et al. |
| 2011/0218327 A1 | 9/2011 | Hansen et al. |
| 2014/0287095 A1 | 9/2014 | Li et al. |
| 2017/0027214 A1 * | 2/2017 | Affolter ............... A23L 33/19 |

* cited by examiner

HIGH PURITY ALPHA LACTALBUMIN AND METHODS OF MAKING

CROSS-REFERENCE TO RELATED APPLICATIONS

This application is a non-provisional of and claims priority to U.S. Provisional App. No. 62/500,354, filed May 2, 2017, entitled "High-Purity Alpha Lactalbumin and Methods of Making, the entire contents of which are herein incorporated by reference for all purposes.

BACKGROUND OF THE INVENTION

α-Lactalbumin (α-LA) is the most prevalent protein in human milk, and therefore an important ingredient for human infant nutrition. Whey protein derived from bovine milk includes α-LA protein that is very similar to human α-LA, making bovine whey protein a primary source of proteins for infant formula. In contrast to human milk, however α-lactalbumin (α-LA) is not the most prevalent whey protein in bovine milk. In cheese whey, the dominant whey protein in bovine milk is ß-lactoglobulin (ß-LG), and there is also a significant fraction of glycomacropeptides (cGMP) that are generated by the enzymatic hydrolysis of the bovine milk's κ-casein protein during cheese making processes. Because virtually no ß-LG or cGMP are present in human milk, it's necessary to reduce their content significantly from bovine whey proteins destined for infant formula.

In contrast to conventional methods of making bovine whey proteins for infant formula by ultrafiltration of cheese whey, one of the methods used for making α-LA enriched WPC for infant formula starts by subjecting whey protein concentrate (WPC) to protease enzymes that selectively hydrolyze the ß-LG and cGMP faster than the α-LA. After an incubation period, the hydrolyzed WPC is then filtered to separate the ß-LG and cGMP depleted whey proteins from the hydrolysates of the ß-LG and cGMP. The enzymatic hydrolysis produces a filtered whey protein retentate with a significantly higher concentration of α-LA relative to the enzymatically depleted concentrations of ß-LG and cGMP. There are however, practical limits on the extent to which enzymatic hydrolysis can remove the ß-LG and cGMP.

While the protease enzymes are chosen for their preference in hydrolyzing ß-LG and cGMP over α-LA, there can still be significant hydrolysis of α-LA as the incubation period progresses. Thus, there is a tradeoff between terminating the incubation too quickly and leaving large amounts of unhydrolyzed ß-LG and cGMP versus continuing the incubation for too long and hydrolyzing too much α-LA along with the ß-LG and cGMP. Furthermore, longer incubation times extend the overall time for the manufacturing process which reduces production rates for the final product. There is also significant inconsistency and unpredictability in factors like temperature and acidity in trying to develop a highly targeted enzymatic hydrolysis of a particular whey protein in a WPC mixture.

Other methods eliminate enzymatic hydrolysis and attempt to separate the various fractions of whey proteins with resin materials using ion exchange that selectively absorbs or attaches a specific protein or subset of whey proteins. While ion exchange yields a high protein ingredient, the process not only is expensive but also creates significant amount of effluents that can cause environmental concerns. There are also challenges releasing the bound proteins from the resin once the whey proteins have passed through the column of resin beads. Processes and resins have also been developed for selectively binding cGMPs in the whey, but these resins do not significantly alter the relative concentrations of α-LA and ß-LG, where are still heavily weighted towards the ß-LG in bovine whey.

Still other methods attempt to selectively purify the fractions of bovine whey proteins using chemical compounds that selectively precipitate a targeted whey protein. For example, some methods call for adding ferric chloride to the WPC at specific temperatures and pHs to precipitate ß-LG. These precipitation methods are not very selective and a significant amount of α-LA gets co-precipitated with the ß-LG. These methods also commonly require the subsequently removal of the precipitating compound, which can make the method cost prohibitive on a commercial scale.

The conventional methods of making bovine whey proteins for infant formula can increase the weight percentage ratio of α-LA to ß-LG from less than 0.6 in the starting WPC where the ß-LG is the most prevalent protein, to between 1 and 3 (e.g., an α/ß weight ratio of 2.0) in the final product. In many instances, the increase in α-LA is enough to provide a commercially viable bovine whey protein source for infant formula. However, there are instances where higher purities of α-LA and even more depleted levels of ß-LG and cGMP are needed. This is especially true for infant formula as ß-LG is a potential infant allergen and cGMP can adversely affect the required amino acid profile for infant formula due to the deficiency of several essential amino acids such as tryptophan and phenylalanine. Thus, there is a need for new methods and products with higher purity levels of α-LA and lower amounts of ß-LG and cGMP proteins than that produced by conventional methods. These and other issues are addressed in the present application.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

BRIEF SUMMARY OF THE INVENTION

Figure 1:
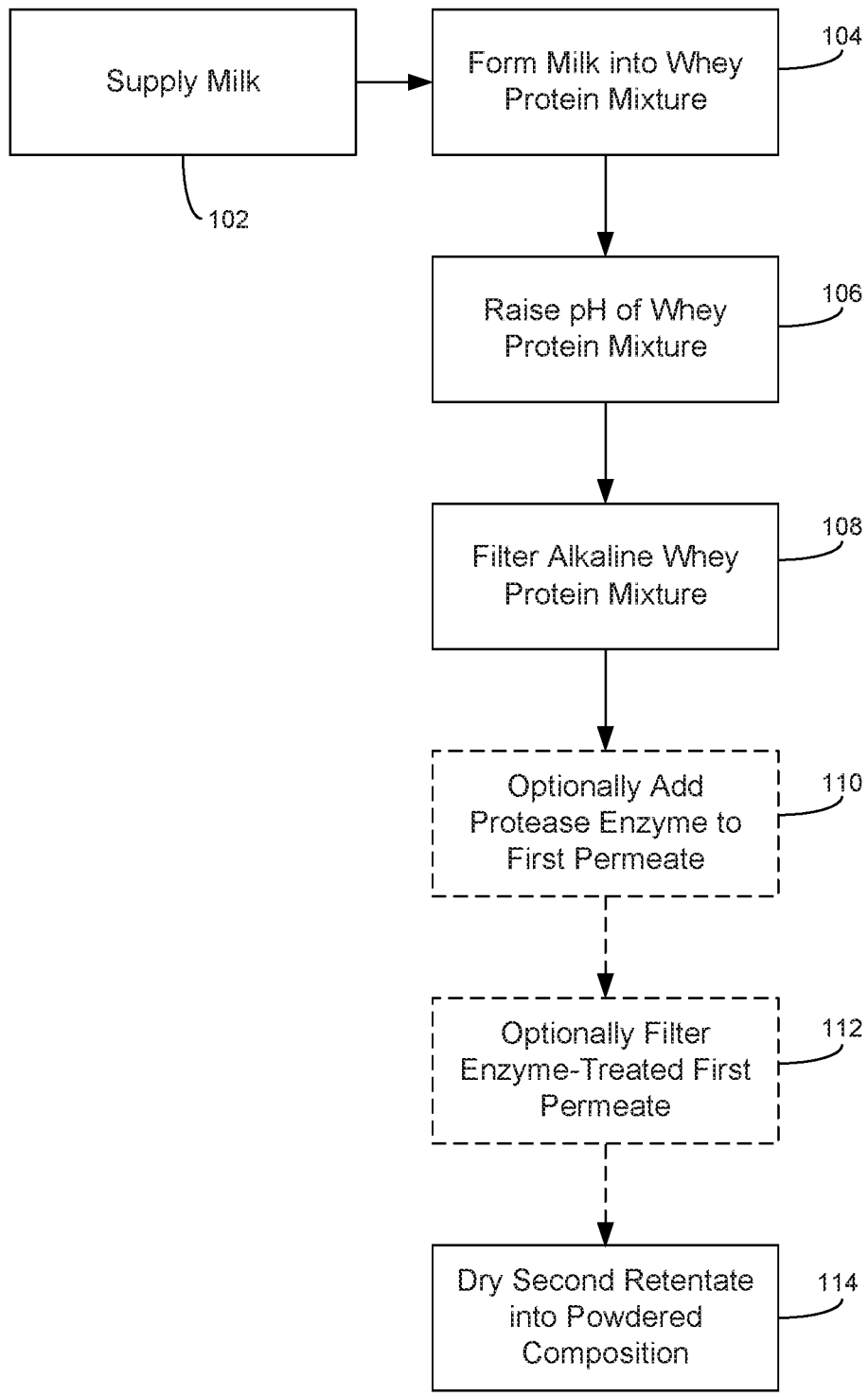
FIG. 1 shows selected steps in methods of making a high-purity α-lactalbumin composition according to embodiments of the invention.

Methods of making high-purity α-lactalbumin compositions are described, as well as embodiments of the compositions. These methods typically start with mixtures of whey proteins that are generated from a dairy source such as raw milk, skim milk, and partially defatted milk, among other dairy sources. The mixture may be made by the microfiltration of milk (e.g., native whey) or the separation of whey from curds during a cheesemaking process (e.g., cheese whey). The whey protein mixtures include α-lactalbumin (α-LA) and ß-lactoglobulin (ß-LG), as well as a significant amount of glycomacropeptides (cGMPs) if the mixture includes cheese whey made from a cheesemaking process. In many instances, the ß-lactoglobulin constitute the largest fraction of the whey protein at 55 wt. % to 60 wt. %, followed by the α-lactalbumin at 15 wt. % to 25 wt. %, and finally the glycomacropeptides at 15 wt. % to 20 wt. % when the whey protein mixture is sourced from cheese whey. Native whey mixtures do not contain cGMP. When the whey protein mixture has an alkaline pH (i.e., greater than 7), it has been discovered that the ß-LG proteins unfold and interact with each other to form soluble aggregates with significantly larger particle sizes than the originally folded proteins. In contrast, the α-LA proteins do not significantly aggregate at these alkaline pHs. The aggregated ß-LG proteins can be physically separated from the unaggregated α-LA proteins, for example by membrane separation, based on the differences in particle size. The present methods first aggregate a large portion of the ß-LG under alkaline conditions (i.e., pH greater than 7) and then separate the aggregated ß-LG from the remaining whey proteins by a first membrane filtration. The resulting α-lactalbumin-enriched compositions can be further enriched by optionally treating them with one or more protease enzymes that selectively hydrolyze residual ß-LG aggregates, and cGMP if present, while leaving the α-LA mostly unhydrolyzed. The larger α-LA proteins are then separated from the enzymatically hydrolyzed ß-LG and cGMP in a second membrane filtration to make the final α-LA-enriched composition. In many instances, the α-LA-enriched composition is dried into a powder.

The present methods can make α-LA compositions having significantly higher purity than conventional methods. Unlike conventional methods that add protease enzymes to a whey protein mixture before separating the ß-LG from the other whey proteins, the present methods aggregate and separate ß-LG from the other whey proteins via filtration before an enzymatic hydrolysis. Adding protease enzymes to an α-LA enriched permeate of the remaining whey proteins permits a more selective hydrolysis of the residual ß-LG aggregates and proteins/polypeptides with an open structure (e.g., cGMP) while leaving the α-LA proteins largely unhydrolyzed. A more selective hydrolysis is permitted by lowering the temperature of the α-LA enriched permeate to 10° C. or less during the enzymatic hydrolysis in a so-called "cold incubation" hydrolysis. The lower temperature slows the hydrolysis rate to a level that reduces the amount of unwanted α-LA hydrolysis before the enzyme activity can be terminated. By removing a significant amount of the ß-LG prior to adding the protease enzymes, the cold incubation of the α-LA enriched permeate can still be terminated in commercially practical amount of time (e.g., less than 4 hours). Fewer ß-LG proteins in the α-LA enriched permeate also result in less ß-LG in the final compositions and a higher weight ratio of α-LA to ß-LG (e.g., an α/ß ratio of 5:1 or more).

When the optional enzymatic hydrolysis step is performed, the present methods use at least two filtration steps to further increase the purity of the α-LA in the composition. Following the termination of the cold-incubation enzymatic hydrolysis in the α-LA enriched permeate, at least one more filtration is performed to separate the intact α-LA proteins from the hydrolyzed whey proteins (e.g., hydrolyzed ß-LG and cGMP). In this filtration, the larger α-LA proteins are separated into the retentate while the hydrolyzed whey proteins end up in the permeate. In contrast, most conventional α-LA purification methods perform just one filtration to separate the α-LA proteins from the hydrolyzed whey proteins.

Embodiments of the invention include methods of making a powdered dairy composition. The methods include providing a whey protein mixture, and adding an alkaline solution to the whey protein mixture to make an alkaline whey protein mixture. In the alkaline mixture, a portion of the ß-lactoglobulin aggregates to form ß-LG aggregates. The alkaline whey protein mixture that includes the ß-LG aggregates may be filtered into (i) a ß-LG aggregate composition and (ii) a α-LA enriched composition. A final α-lactalbumin enriched composition sourced from the α-LA enriched composition into the powdered dairy composition. As noted above, when additional enrichment of the α-LA levels is desired, optional steps may be included to add a protease enzyme to the α-LA enriched composition to hydrolyze at least a portion of the residual ß-LG, and glycomacropeptides if present, into enzymatically hydrolyzed fragments. The enzymatically treated α-LA enriched composition may be filtered into the final α-lactalbumin enriched composition with a higher concentration of α-LA proteins and a permeate that has the enzymatically hydrolyzed protein fragments. The concentration of α-lactalbumin protein in the powdered dairy compositions is at least 70 wt. % on a protein basis.

Embodiments of the invention also include high-purity α-lactalbumin dairy compositions. The compositions may include 50 wt. % or more, 60 wt. % or more, 70 wt. % or more, 80 wt. % or more whey proteins (as measured on a dry basis). The whey proteins may have a 5:1 or more weight ratio of α-lactalbumin to ß-lactoglobulin. The compositions may also include 1 wt. % or less glycomacropeptides (as measured on a dry basis).

Embodiments of the invention still further include enriched α-lactalbumin compositions. An enriched α-lactalbumin dairy composition may be added from an α-lactalbumin containing filtration retentate, wherein the α-lactalbumin containing filtration retentate is formed from an enzymatically treated filtration permeate that was filtered into the filtration retentate and a glycomacropeptide fragment-containing permeate, wherein the enzymatically treated filtration permeate may be formed by: (i) filtering a treated whey protein solution into a first α-LA permeate and a first ß-LG retentate, wherein the treated whey protein solution is formed by adding an alkaline solution to a whey protein solution, and wherein the alkaline solution increases the pH of the whey protein solution to greater than 7. (ii) adding a protease enzyme to the first α-LA permeate to make the enzymatically treated first filtration permeate. (iii) subjecting the first filtration permeate to a second filtration to make an α-LA enriched second retentate and a second permeate that includes hydrolyzed glycomacropeptides/ß-LG fragments.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

Additional details are provided for methods and systems to make high-purity α-lactalbumin compositions. The methods and systems start with a source of whey protein such as sweet whey, whey protein concentrate, or whey protein isolate derived from cow's milk and convert it into dairy compositions with high purity levels of α-LA and low levels of ß-lactoglobulin (ß-LG) and glycomacropeptides (cGMPs) relative to the starting whey source. For example, bovine whey protein concentrate (WPC) typically starts with 55-65 wt. % ß-LG, 15-25 wt. % α-LA, and 15-20 wt. % cGMPs. The present methods and systems produce dairy compositions from the starting WPC that has a weight ratio of the α-LA to the ß-LG of 5:1 or more, changing the α-LA to the most prevalent whey protein in the dairy composition. They also reduce the concentration of cGMPs in the composition to less than 1 wt. % on a dry basis. In some embodiments, the source of whey proteins may come directly from milk that has been microfiltered to form a micellar casein retentate and native whey permeate. In the case of native whey the mixture of proteins includes 45-55 wt. % ß-LG, 15-25 wt. % α-LA, and about 0 wt. % cGMP. Native whey may also include 0-50 wt. % ß-casein.

The methods and systems include combinations of alkaline aggregation, selective enzymatic hydrolysis, and at least two filtrations to increase the concentration of the α-LA relative to the other primary constituents in the starting whey protein source. The combination and order of these steps result in dairy compositions that have a higher purity of α-LA than possible with conventional methods and systems for making α-LA protein products.

Exemplary Methods of Making High-Purity α-LA Compositions

Methods of making high-purity α-lactalbumin compositions are described, as well as embodiments of the compositions. These methods typically start with mixtures of whey proteins that include α-lactalbumin (α-LA), ß-lactoglobulin (ß-LG), and glycomacropeptides (cGMPs). In many instances, the ß-lactoglobulin constitutes the largest fraction of the whey protein, followed by the α-lactalbumin, and finally the glycomacropeptides. The present methods first aggregate a large portion of the ß-LG under alkaline conditions (i.e., pH greater than 7) and then separate the aggregated ß-LG from the remaining whey proteins. The remaining whey proteins are then treated with one or more protease enzymes that selectively hydrolyze the cGMPs and residual ß-LG while leaving the α-LA mostly unhydrolyzed. The larger α-LA proteins are then separated from the enzymatically hydrolyzed cGMPs and ß-LG to make the high-purity α-LA compositions. In many instances, the separated α-LA is dried into a powder.

FIG. 1 shows selected steps in methods 100 of making a high-purity α-LA composition according to embodiments of the invention. The methods 100 include step 102 of supplying starting milk that is formed into a whey protein mixture in step 104. The starting milk may include a variety of bovine milks such as whole milk, reduced-fat milk, low-fat milk, skim milk, and combinations of two or more of these types of milk. In an alternate description, the starting milk may include milk having a milkfat content ranging from 4.5 wt. % to 0 wt. %. Specific examples include milk with 4.5 wt. % to 2 wt. % milkfat, 2 wt. % to 1 wt. % milkfat, 1 wt. % to 0.5 wt. % milkfat, and 0.5 wt. % or less milkfat.

Staring bovine whole milk contains approximately 3.3 wt. % protein, 3.4 wt. % fat, 4.9 wt. % carbohydrate (primarily lactose), and 0.7 wt. % minerals (including calcium). The proteins in the bovine milk include about 80 wt. % casein proteins and about 20 wt. % whey proteins. As noted above, the whey proteins include predominantly ß-LG and α-LA. The starting bovine milk may be used in a cheesemaking process that divides the milk proteins into primarily casein-containing cheese curds and primarily whey protein-containing liquid whey. In most enzymatic cheesemaking processes, the casein-containing cheese curds are formed by hydrolyzing a c-terminal glycomacropeptide (cGMP) protein from the starting κ-casein proteins. The cGMP is released into the liquid whey and typically makes up approximately 15-20 wt. % of the protein content of the whey. In the case of native whey proteins that have not been exposed to the hydrolysis enzymes, there is little or no cGMP.

The raw whey generated from the cheesemaking process may be referred to as "sweet whey" when the cheesemaking process uses rennet enzymes like chymosin, and "acid whey" when acids are used to form the curds. The pH of sweet whey typically ranges from about 5.6 to 6.6, while the pH of acid whey typically ranges from 4.3 to 4.6. Raw whey is typically 93 wt. % to 95 wt. % water, which gives it a total solids concentration ranging from 5 wt. % to 7 wt. %. In addition to the proteins, the predominant ingredient in the raw whey is carbohydrates, primarily lactose, which can account for as much as 60-80% (e.g., 75%) by dry weight. The raw whey may also include fats, vitamins, and minerals such as calcium and sodium. The raw whey may be converted into more pure forms of whey protein as part of step 104.

The more pure forms of whey protein that make up the whey protein mixture formed in step 104 may include whey protein concentrate (WPC) and whey protein isolate (WPI). Exemplary sources of the whey protein used in the WPC and WPI include native whey proteins present in milk and whey proteins that have been separated from cheese curd during a cheesemaking process. The whey protein concentrate may be formed by membrane filtration and/or chromatography that separates the whey proteins from the carbohydrates. In WPC, the whey proteins are normally purified to about 25 wt. % to 89 wt. % protein on a dry basis of the concentrate. In whey protein isolates the whey proteins are purified even more using membrane filtration (e.g., microfiltration, ultrafiltration) and/or diafiltration techniques that can bring the protein content in the WPI to about 90 wt. % or more (e.g., 92 wt. % to 99 wt. %) on a dry basis. The WPC and/or WPI may be supplied as an aqueous slurry or a dry powder to the whey protein mixture formed in step 104.

In addition to purifying, the starting whey may be pasteurized and/or clarified. Pasteurization may involve heating the starting whey to temperatures of 145° F. to 150° F. for a period of about 30 minutes, or heating the starting whey to temperatures of 160-165° F. for a period of less than a minute (e.g., about 15 seconds). Pasteurization methods may also include heating the starting whey at very high temperatures 280-302° F. for very short periods of 1 to 2 seconds in a process commonly referred to as ultra-high-temperature (UHT) pasteurization. Clarifying involves the removal of larger sized particles from the starting whey, such as residual curd particles. Exemplary techniques for clarifying the starting whey include (i) straining or filtering the starting whey through a filter and/or sieve having a pore size of, for example 25-100 µm, and (ii) centrifuging the starting whey and extracting the clarified liquid from the solid sludge.

The formation of the whey protein mixture in step 104 may involve diluting the above-described WPC or WPI with water until the protein concentration reaches 5 wt. % to 15 wt. % of the weight of the mixture. Aqueous dilution also reduces the total solids content of the starting WPC or WPI to, for example, a range of 6% to 20% of the weight of the mixture. Other exemplary dilution ranges include (i) 8% to 12% total solids content (TS) and (ii) 10% to 11% TS. The water used to dilute the starting WPC or WPI may be untreated or treated to remove some or all of the salt and mineral content. Examples include deionized water, distilled water, filtered water, and tap water, among other types of water.

Once formed, the whey protein mixture is made more alkaline by raising the pH in step 106. Raising the pH may involve adding to the whey protein mixture an alkaline compound such as a food-grade hydroxide compound (e.g., sodium hydroxide, potassium hydroxide, calcium hydroxide, ammonium hydroxide, etc.). The alkaline compound is typically added as an alkaline solution (i.e., an aqueous solution) to the whey protein mixture. Alternatively, the pH may be raised by adding the alkaline compound as a solid (e.g., a dry powder) instead of a liquid solution. The pH is raised to make the whey protein mixture alkaline (i.e., greater than 7.0). In some examples, the pH is raised to make the whey protein mixture very alkaline, with an alkaline solution added until the mixture has a pH of greater than 8, greater than 9, greater than 10, greater than 10.5, etc. Other pH ranges include 7 to 12; 7 to 11; 7.5 to 10.5; 8 to 10.5; 9 to 10.5; and 10 to 10.5, among other pH ranges.

Raising the pH in step 106 may be done while the whey protein mixture is at room temperature (e.g., 68-72° F.) or above, or when the mixture is cold (e.g., 50° F. or less). If the alkaline whey protein mixture starts at room temperature or above, it may be cooled to a temperature of 50° F. or less (e.g., 50-40° F.) and agitated. Under conditions of alkaline pH and reduced temperature, the ß-LG proteins in the mixture will aggregate into larger clusters and suspended particulates in about 1 minute or more (e.g., 1-5 minutes). The aggregation of a significant portion of the ß-LG allows them to be more easily separated from the α-LA proteins in the mixture.

The alkaline whey protein mixture containing the aggregated ß-LG proteins may be filtered in step 108. The net result is to separate the alkaline whey protein mixture into (i) a ß-LG enriched retentate and (ii) a α-LA enriched permeate, which can also be thought of as a ß-LG depleted permeate. The filtration may be done using ultrafiltration (UF) and/or diafiltration (DF). Ultrafiltration techniques may include cross-flow filtration of the alkaline whey protein mixture through spiral-wound, plate and frame, and/or ceramic membrane modules. The spiral-wound membrane module may include (i) a perforated center conduit through which a permeate can infiltrate and travel, and (ii) one or more sheets wrapped around the center conduit. At least one of the sheets is an ultrafiltration membrane that blocks the migration of the retentate while permitting the radial transfer of the liquid permeate to and through the center conduit. The ultrafiltration membrane sheet may be made from an organic polymer or inorganic material. Examples of suitable organic polymers include one or more of cellulose acetate, polysulfone, polyvinylidene fluoride, polyethersulfone, polyesters, and polyamide, among other types of organic polymers. Suitable inorganic materials may include mineral and/or ceramic based materials, among other types of inorganic materials.

Examples of the filtration step 108 include introducing the alkaline whey protein mixture to a spiral-wound, flat-sheet, or ceramic ultrafiltration membrane having a molecular weight cutoff (MWCO) that blocks the passage of the aggregated ß-LG proteins while permitting the transfer of the non-aggregated α-LA and cGMP through the membrane. The molecular weight of bovine ß-LG is approximately 18.4 kDa, so a membrane may be selected to provide a MWCO that provides a 90% retention of the ß-LG (e.g., 15 kDa or more, 16 kDa or more, 17 kDa or more, 18 kDa or more, 19 kDa or more, 20 kDa or more, 21 kDa or more, etc).

Bovine ß-LG is larger than α-LA (14.2 kDa) or cGMP (6.7-9.6 kDa), however the similar molecular weights are challenging for effective separation by ultrafiltration. Thus, embodiments also include ultrafiltration membranes with MWCOs set for capturing the aggregated ß-LG proteins in the retentate while passing the unaggregated proteins to the permeate with the α-LA and cGMP. The MWCOs may be set for a multiple of the 18.4 kDa molecular weight of the unaggregated ß-LG protein (e.g., 36.8 kDa or more (×2), 55.2 kDa or more (×3), 73.6 kDa or more (×4), 92 kDa or more (×5), etc.). Exemplary MWCOs may range from 40 kDa to 500 kDa, depending on the extent of ß-LG protein aggregation in the alkaline whey protein mixture. The filtration step 108 may also include diafiltration by introducing water to the ultrafiltration membrane during and/or after the introduction of the alkaline whey protein mixture to further separate the ß-LG-enriched retentate from the α-LA-enriched permeate. The ß-LG-enriched retentate may be dried and formed into ß-LG-enriched product.

Alternate examples of the filtration step 108 may also include ultrafiltration techniques that use dead-end filtration, where the alkaline whey protein mixture meets a membrane barrier that holds particles larger than the membrane pore size back as the ß-LG-enriched retentate while permitting smaller particles and liquid through as the α-LA enriched permeate. The UF membrane barrier may have a plate-and-frame design that holds the membrane itself as a flat sheet that intersects the flow of the alkaline whey protein mixture. In some examples, the membrane barrier can be made of an organic polymer such as cellulose acetate, polysulfone, polyvinylidene fluoride, polyethersulfone, polyesters, and polyamide, among other types of organic polymers, or alternatively the membrane barrier can be made of an inorganic ceramic. Exemplary MWCOs include a range from 40 to 500 kDaltons (e.g., 50 to 100 kDa), depending upon the extent of aggregation in the ß-LG proteins, the type of membrane used, and whether the membrane is charged or non-charged.

One or more protease enzymes are added to the α-LA-enriched permeate in step 110. The protease enzyme is chosen for selectively hydrolyzing the residual ß-LG proteins not caught in the aggregated ß-LG retentate and the cGMP over the α-LA proteins. The protease enzymes may be sourced from microorganisms, fungi, plants, and/or animals. For example, the protease enzyme may be sourced from a fungi of the genus *Aspergillus*, a bacteria of the genus *Bacillus* (e.g., *Bacillus subtilis*), and animal-derived protease enzymes such as trypsin and chymotrypsin, among others. The protease enzymes may be added in a single aliquot mixed into the whey protein mixture, or in a plurality of additions. The enzymes may also be continuously streamed into the stirred or agitated whey protein mixture. The enzymes may be added at concentration levels ranging from 0.2 wt. % to 1 wt. % (e.g., about 0.5 wt. %) of the weight of the protein in the permeate.

In optional embodiments, one or more protease enzymes are added to a cold permeate that has a temperature of 10° C. or less, and remains at a cold temperature for the duration of the enzymatic hydrolysis of the proteins. This cold-incubation hydrolysis can last for a period of 5 hours or less (e.g., from 1 to 60 minutes). The duration of the hydrolysis is significantly shorter than conventional enzymatic hydrolyses that can take 24 hours or longer at cold incubation temperatures. The shorter hydrolysis times are attributable to the removal of most of the ß-LG proteins before the protease enzymes are introduced to the α-LA-enriched permeate in optional step 110. The cold incubation can end in a short period of time by flash heating the permeate. For example the temperature of the hydrolyzing permeate can be raised to 90° C.–100° C. within 15 seconds to 10 minutes to abruptly terminate the activity of the protease enzymes.

The pH of the α-LA-enriched permeate may be around neutral (e.g., about 7) during the cold incubation hydrolysis. As noted above, the pH of the alkaline whey protein mixture may be adjusted closer to neutral by the addition of an acid following the aggregation of the ß-LG proteins. Alternatively, an acid may be added just to the α-LA-enriched permeate following the filtration step 108. In still other embodiments, no acid is added to the alkaline whey protein mixture or α-LA-enriched permeate, and the enzymatic hydrolysis occurs in an alkaline permeate (i.e., pH greater than 7).

In some embodiments, the end-point of the cold-incubation hydrolysis comes at a predetermined time (e.g., 1 to 60 minutes), while in further embodiments the end-point can be a function of one or more measured conditions such as pH, ß-LG concentration, cGMP concentration, and/or α-LA concentration. For example, if the concentration of α-LA proteins drops by more than 1 wt. %, 2 wt. %, 5 wt. %, or 10 wt. %, among other percentage drops, the activity of the protease enzymes is terminated. In another example, of the concentration of ß-LG and/or cGMP drops below a threshold level (e.g., 5 wt. % or less, 3 wt. % or less, 2 wt. % or less, 1 wt. % or less, 0.5 wt. % or less, etc. by total weight of the protein) the enzyme activity is terminated.

In some embodiments, the hydrolyzed permeate may undergo an optional second filtration in step 112. This filtration may be another ultrafiltration and/or diafiltration similar to the one described in step 108 above. However, in this filtration the unhydrolyzed α-LA proteins are larger than the enzymatically hydrolyzed fragments ß-LG and cGMP, and captured in an α-LA-enriched retentate. At the same time, the smaller hydrolysis fragments of the ß-LG and cGMP pass through the ultrafiltration membrane and become part of α-LA-depleted permeate. The MWCO for the ultrafiltration membrane is set to permit the passing of the majority of the hydrolysis fragments (including fragments of any hydrolyzed α-LA proteins), while blocking the passage of the un-hydrolyzed α-LA proteins. The molecular weight of bovine α-LA is about 14.2 kDa, so a membrane may be selected to provide a MWCO that provides a 90% retention of the α-LA while also permitting the passage of most or all the hydrolyzed fragments ß-LG and cGMP. Exemplary MWCO ranges include 5-15 kDa, 8-14 kDa, etc.

The α-LA-enriched retentate is dried into a powdered composition in step 114. Exemplary drying methods include spray drying where the slurried α-LA-enriched retentate is atomized by passing through a nozzle. The atomized retentate makes contact with a hot drying gas (e.g., filtered air, nitrogen, etc.) having a temperature ranging from 20-220° C. The spray-dried α-LA-enriched powdered composition typically have particle sizes ranging from 10 to 500 µm (e.g., 100-300 µm).

Figure 2:
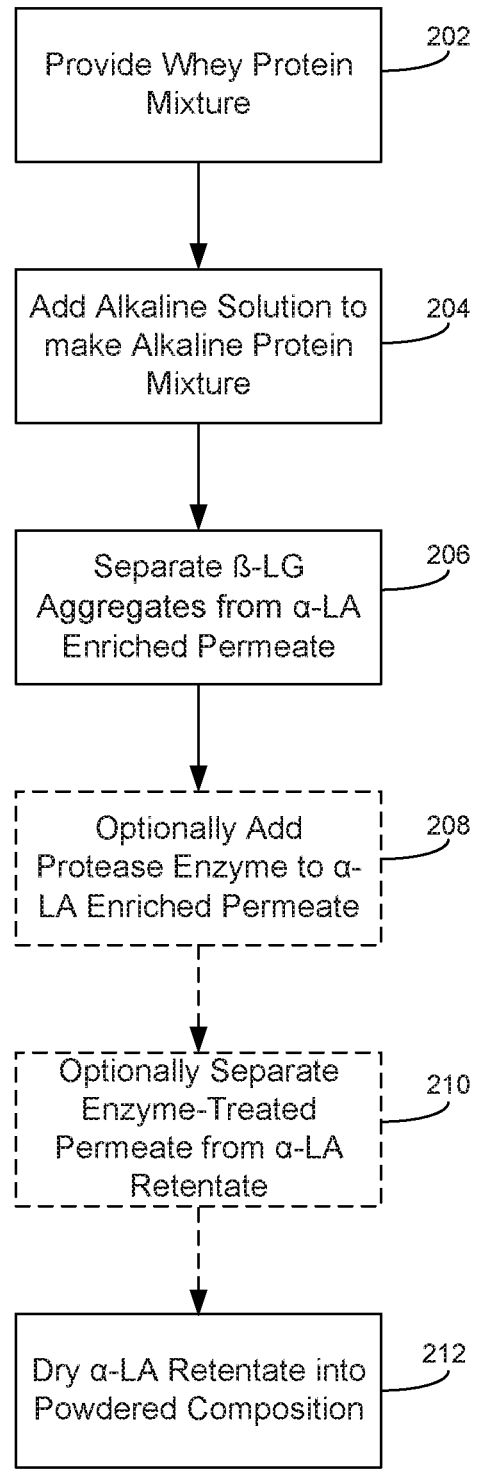
FIG. 2 shows selected steps in additional methods of making high-purity α-lactalbumin compositions according to embodiments of the invention.

FIG. 2 shows selected steps in methods 200 of making a high-purity α-LA composition according to embodiments of the invention. The methods 200 include a step 202 of providing a whey protein mixture. Exemplary whey protein mixtures include whey protein concentrate (e.g., WPC 80) diluted with water to a total solids concentration of 10-12 wt. %. In some examples, the whey protein mixture is a solution where the proteins are fully dissolved in the added water, while in additional examples the whey protein mixture includes particles of undissolved whey proteins in the water, such as a slurry, suspension, and/or colloid.

An alkaline solution may be added to the whey protein mixture to make the mixture alkaline (i.e., pH greater than 7) in step 204. Exemplary pH targets for the alkaline protein mixture include 7.5 or more, 7.5-12, and 10-10.5, among other target pHs. Before or after adding the alkaline solution, the whey protein mixture may be cooled from room temperature (or above) to a temperature below room temperature (i.e., below about 23° C.). Exemplary temperatures include 10° C. or less, 10° C. to 7° C., etc. The alkaline pH and colder temperatures facilitate the aggregation of the ß-LG proteins into aggregates that are easier to separate from the intact α-LA proteins.

The aggregated ß-LG proteins are separated from the α-LA and cGMP in step 206. Exemplary methods for separating the ß-LG aggregates includes ultrafiltration with different MWCO membranes depending on the extent of the aggregation in the ß-LG protein. The filtration techniques separate the alkaline whey protein mixture into a retentate that includes the ß-LG aggregates and a α-LA enriched permeate that includes the α-LA, residual ß-LG, and cGMP.

In some embodiments, protease enzymes may be added to the permeate in optional step 208. The protease enzymes are chosen for their ability to selectively hydrolyze the residual ß-LG proteins that pass through the membrane into the permeate, as well as the cGMP, while hydrolyzing the α-LA protein at a significantly lower rate. The selective hydrolysis is further facilitated by conditions in the permeate such as temperature and pH. The enzymatic hydrolysis may be conducted at temperatures colder than room temperature (e.g., cold incubation temperatures of 10° C. to 7° C.) that slows the rate of hydrolysis in order to more easily hit a termination point that represents an acceptable balance between (i) the amount of ß-LG and cGMP that are hydrolyzed, and (ii) the amount of α-LA protein that remain unhydrolyzed. The pH may be adjusted to be at or near the fastest hydrolysis rates for the protease enzyme (or enzymes). The pH may be adjusted by the addition of acids and/or bases to the permeate before or during the enzymatic hydrolysis.

Cold-incubation enzymatic hydrolysis times may range from a period of several hours (e.g. 5 hours or less) to periods of minutes (e.g., from 1 to 60 minutes). The hydrolysis period may end abruptly by flash heating the permeate to inactivate the protease enzymes. Exemplary flash heating techniques may include raising the temperature of the permeate to 90° C.-100° C. within 15 seconds to 10 minutes. The temperature of the flash-heated permeate may be just as quickly ramped down to room temperature or below to prevent the denaturation of the unhydrolyzed α-LA proteins.

In some embodiments, the enzyme-treated permeate may undergo a separation of the enzymatically hydrolyzed ß-LG and cGMP from the unhydrolyzed α-LA protein in optional step 210. Exemplary separation methods include ultrafiltration that captures the larger, unhydrolyzed α-LA protein in an α-LA-enriched retentate while passing the hydrolyzed ß-LG and cGMP in an α-LA-depleted permeate. As noted above, the MWCO for the ultrafiltration membrane is set to permit the passage of the majority of the ß-LG and cGMP hydrolysis fragments, but block the passage of most or all of the un-hydrolyzed α-LA protein. Exemplary MWCOs that provide at least a 90% retention of the un-hydrolyzed α-LA protein include ranges of 5-15 kDa, 8-14 kDa; etc. While the α-LA-enriched retentate may contain some residual ß-LG and cGMP, the α/ß weight ratio of α-LA to ß-LG protein in the retentate may range from 3:1 or more, 4:1 or more, 5:1 or more, etc. In addition, the weight percent cGMP in the retentate is less than 1 wt. % on a dry basis.

The α-LA-enriched retentate is dried into a powdered composition in step 212. Drying techniques may include spray drying, as discussed above. In alternate embodiments, the α-LA-enriched retentate is not dried and instead made as an aqueous paste or slurry. In still additional embodiments, the α-LA-enriched retentate is diluted with water to form an aqueous suspension or solution.

Figure 3:
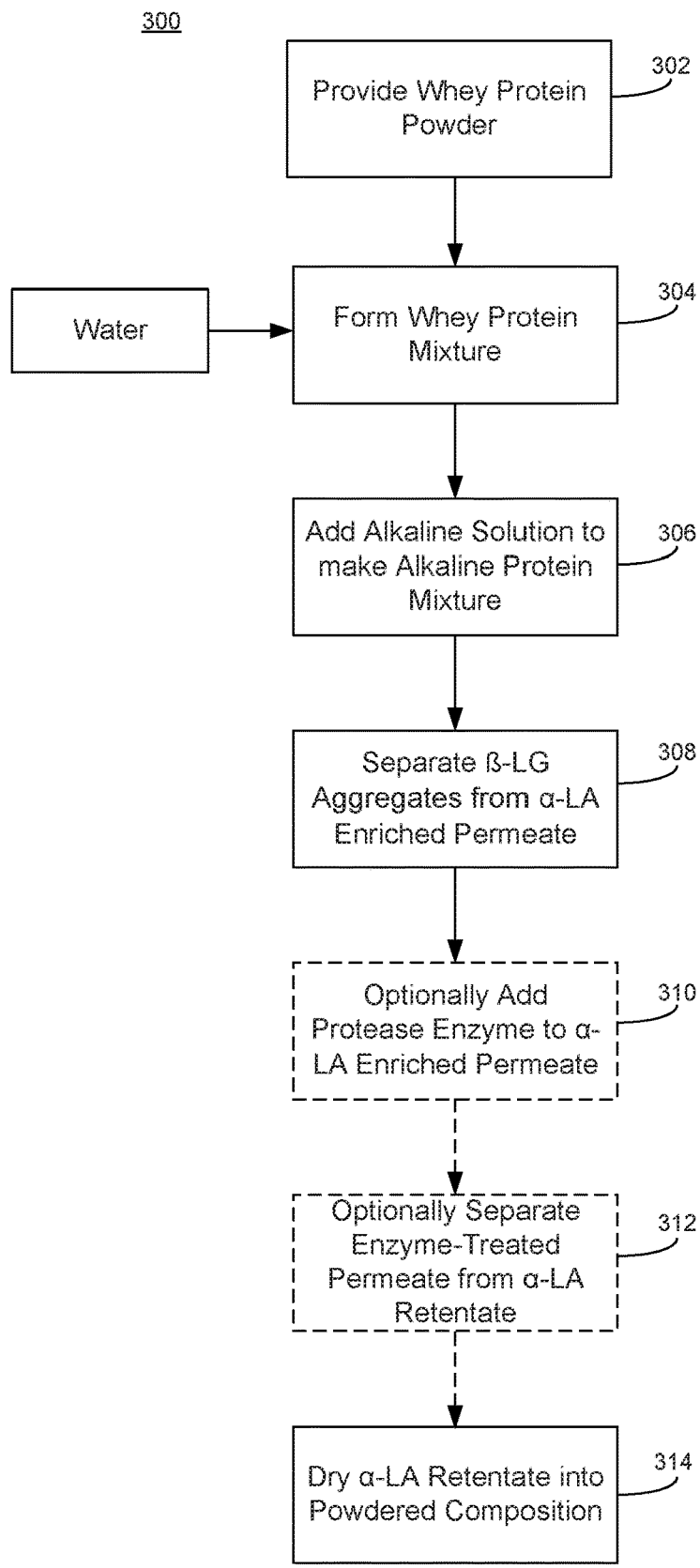
FIG. 3 shows selected steps in further methods of making high-purity α-lactalbumin compositions according to embodiments of the invention.

FIG. 3 shows selected steps in additional methods 300 of making a high-purity α-LA composition according to embodiments of the invention. The methods 300 include a step 302 of providing a whey protein powder (e.g., WPC 80, WPI, etc.) and combining it with water. The combination forms a whey protein mixture 304 with a total solids concentration of, for example, 10-12 wt. %. In some examples, the whey protein mixture is a solution where the proteins are fully dissolved in the added water, while in additional examples the whey protein mixture includes particles of undissolved whey proteins in the water, such as a slurry, suspension, and/or colloid.

An alkaline solution may be added to the whey protein mixture to make the mixture alkaline (i.e., pH greater than 7) in step 306. Exemplary pH targets for the alkaline protein mixture include 7.5 or more, 7.5-12, and 10-10.5, among other target pHs. Before or after adding the alkaline solution, the whey protein mixture may be cooled from room temperature (or above) to a temperature below room temperature (i.e., below about 23° C.). Exemplary temperatures include 10° C. or less, 10° C. to 7° C., etc. The alkaline pH and colder temperatures facilitate the aggregation of the ß-LG proteins into aggregates that are easier to separate from the intact α-LA proteins.

The aggregated ß-LG proteins are separated from the α-LA and cGMP in step 308. Exemplary methods for separating the ß-LG aggregates includes ultrafiltration with different MWCO membranes depending on the extent of the aggregation in the ß-LG protein. The filtration techniques separate the alkaline whey protein mixture into a retentate that includes the ß-LG aggregates and a α-LA enriched permeate that includes the α-LA, residual ß-LG, and cGMP.

In some embodiments, protease enzymes may be added to the permeate in optional step 310. The protease enzymes are chosen for their ability to selectively hydrolyze the residual ß-LG proteins that pass through the membrane into the permeate, as well as the cGMP, while hydrolyzing the α-LA protein at a significantly lower rate. The selective hydrolysis is further facilitated by conditions in the permeate such as temperature and pH. The enzymatic hydrolysis may be conducted at temperatures colder than room temperature (e.g., cold incubation temperatures of 10° C. to 7° C.) that slows the rate of hydrolysis in order to more easily hit a termination point that represents an acceptable balance between (i) the amount of ß-LG and cGMP that are hydrolyzed, and (ii) the amount of α-LA protein that remain unhydrolyzed. The pH may be adjusted to be at or near the fastest hydrolysis rates for the protease enzyme (or enzymes). The pH may be adjusted by the addition of acids and/or bases to the permeate before or during the enzymatic hydrolysis.

Cold-incubation enzymatic hydrolysis times may range from a period of several hours (e.g. 5 hours or less) to periods of minutes (e.g., from 1 to 60 minutes). The hydrolysis period may end abruptly by flash heating the permeate to inactivate the protease enzymes. Exemplary flash heating techniques may include raising the temperature of the permeate to 90° C.-100° C. within 15 seconds to 10 minutes. The temperature of the flash-heated permeate may be just as quickly ramped down to room temperature or below to prevent the denaturation of the unhydrolyzed α-LA proteins.

In some embodiments, the enzyme-treated permeate may undergo a separation of the enzymatically hydrolyzed ß-LG and cGMP from the unhydrolyzed α-LA protein in optional step 312. Exemplary separation methods include ultrafiltration that captures the larger, unhydrolyzed α-LA protein in an α-LA-enriched retentate while passing the hydrolyzed ß-LG and cGMP in an α-LA-depleted permeate. As noted above, the MWCO for the ultrafiltration membrane is set to permit the passage of the majority of the ß-LG and cGMP hydrolysis fragments, but block the passage of most or all of the un-hydrolyzed α-LA protein. Exemplary MWCOs that provide at least a 90% retention of the un-hydrolyzed α-LA protein include ranges of 5-15 kDa, 8-14 kDa; etc. While the α-LA-enriched retentate may contain some residual ß-LG and cGMP, the α/ß weight ratio of α-LA to ß-LG protein in the retentate may range from 3:1 or more, 4:1 or more, 5:1 or more, etc. In addition, the weight percent cGMP in the retentate is less than 1 wt. % on a dry basis.

The α-LA-enriched retentate is dried into a powdered composition in step 314. Drying techniques may include spray drying, as discussed above. In alternate embodiments, the α-LA-enriched retentate is not dried and instead made as an aqueous paste or slurry. In still additional embodiments, the α-LA-enriched retentate is diluted with water to form an aqueous suspension or solution.

Figure 4:
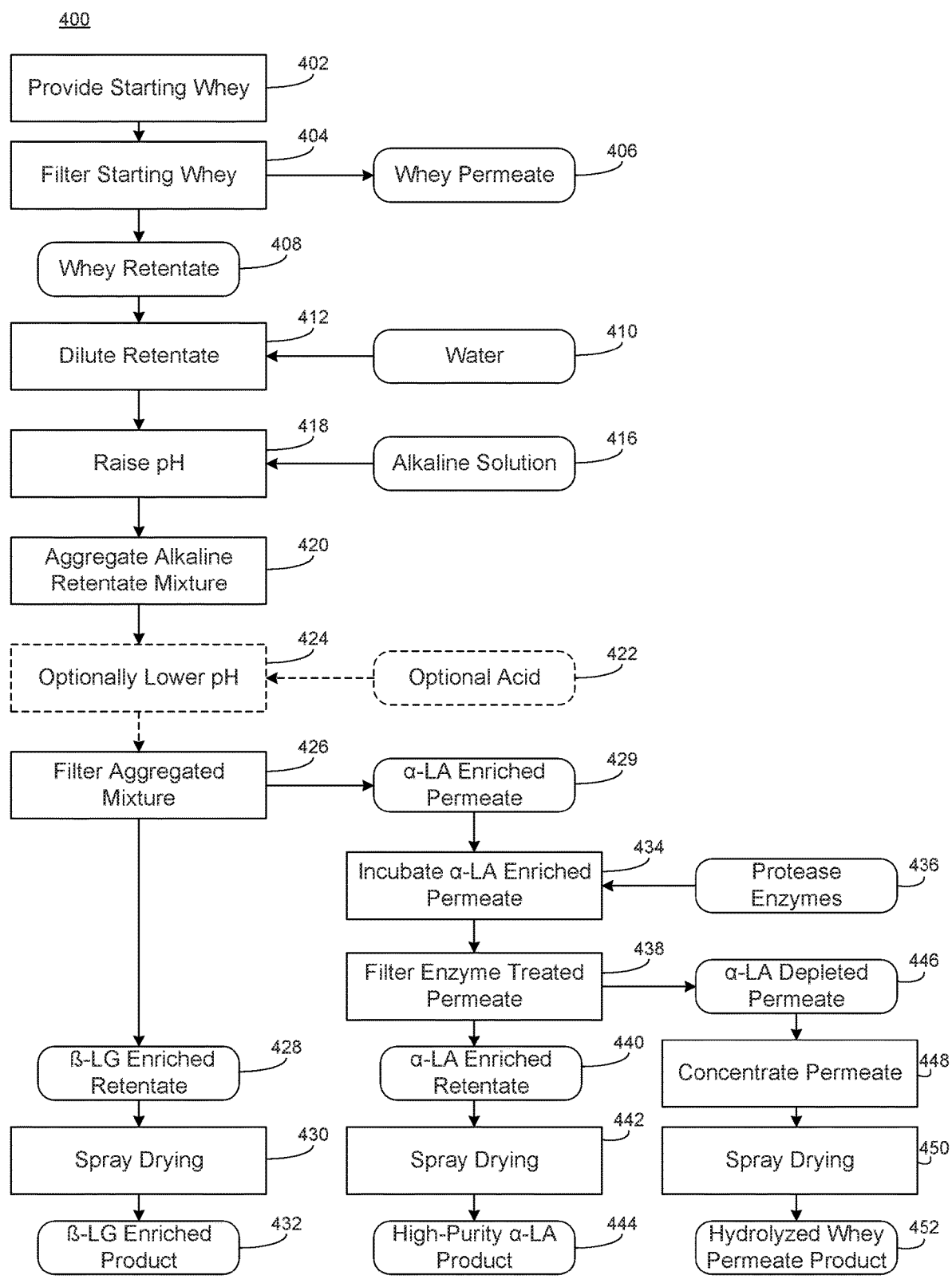
FIG. 4 shows selected steps in methods of making ß-lactoglobulin enriched products, high-purity α-lactalbumin products, and hydrolyzed whey permeate products according to embodiments of the invention.

FIG. 4 shows selected steps in a method 400 of making ß-lactoglobulin enriched products, high-purity α-LA products, and hydrolyzed whey permeate products according to embodiments of the invention. The method 400 includes providing a source of starting whey in step 402. The starting whey may be derived from a cheesemaking process that separates a starting milk into (i) the curds used to make the cheese, and (ii) the liquid whey byproduct, that includes dairy sugars (e.g., lactose), minerals (e.g., calcium, sodium, potassium), and cGMP enzymatically cleaved from the starting κ-casein, in addition to the whey proteins. The starting whey may also include curd particulates and other solids that infiltrated the liquid whey as it was being separated from the curds.

The starting whey is filtered in step 404 into a whey permeate 406 and whey retentate 408. This filtration step may include ultrafiltration to separate the larger proteins from the smaller dairy sugars and minerals. An ultrafiltration membrane having a MWCO that holds back the whey proteins in the retentate 408 while passing the dairy sugars and minerals in the permeate 406 may be used. Diafiltration may also be used to remove additional sugars and minerals from the whey retentate 408 and further concentrate the proteins. Embodiments include having the whey retentate 408 represent a whey protein concentrate (WPC) where the weight of the proteins represent 25 wt. % to 89 wt. % (e.g., WPC 25 to WPC 89) of the total solids in the retentate 408.

The whey retentate 408 may be diluted with water 410 in step 412. Embodiments include diluting the whey retentate 408 to a total solids concentration of 9% to 11% (e.g., 10.5%) in the diluted whey retentate. The dilution may be done by adding water or an aqueous solution to the whey retentate 408. Alternatively, the whey retentate 408 may be added to the water or aqueous solution.

The pH of the diluted whey retentate is raised in step 418 by adding an alkaline solution 416 to the diluted whey retentate. Exemplary alkaline solutions include alkaline metal hydroxide salts such as sodium hydroxide (NaOH) and potassium hydroxide (KOH). The addition of the alkaline solution raises the pH of the diluted whey retentate to greater than 7. Exemplary pH ranges include greater than 7, greater than 8, greater than 9, greater than 10, 7.5 to 12, 8 to 10.5, 9 to 10.5, etc. The alkaline solution may be added to the diluted whey retentate at (i) a temperature that is at or above room temperature or (ii) at a temperature below room temperate (e.g., 10° C. or less, 10° C. to 7° C., etc.). If the pH alkaline solution is added to the diluted whey retentate at or above room temperature, the resulting alkaline whey protein mixture is cooled below room temperature to facilitate the aggregation of the ß-LG proteins in the mixture.

The ß-LG proteins are aggregated in the cold, alkaline whey protein mixture in step 420. As noted above, the aggregation times are normally 1 minute or more (e.g., 1-5 minutes) to permit the individual ß-LG proteins to aggregate into clusters of 2 or more ß-LG proteins. Because the conditions in the alkaline whey protein mixture favor the selective aggregation of the ß-LG proteins over the α-LA proteins the two types of whey proteins are more easily separated.

In some embodiments, the alkaline whey protein mixture containing the aggregated ß-LG proteins may be adjusted back to a more neutral or acidic pH as shown in optional step 424. Lowering the pH may be accomplished by adding an acid 422 to the alkaline whey protein mixture. Exemplary acids include food-grade organic acids such as citric acid. In other embodiments, the alkaline whey protein mixture is kept alkaline when the aggregated ß-LG proteins are separated from the α-LA proteins.

The aggregated ß-LG proteins are separated from the α-LA proteins in step 426. The separation may be accomplished by ultrafiltration of the alkaline whey protein mixture into a ß-LG-enriched retentate 428 and a α-LA enriched permeate 429 that includes the majority of the α-LA proteins from the mixture. The ß-LG-enriched retentate 428 may be spray dried in step 430 to form a powdered ß-LG-enriched product 432. The ß-LG-enriched product 432 includes more than 70 wt. % ß-LG on a protein basis and has a weight ratio of ß-LG proteins to α-LA proteins (ß/α) of 5:1 or more. Commercial uses of the ß-LG-enriched product 432 include incorporation into yogurt, hydrolyzed whey protein, and nutritional food products, among other uses.

As noted above, the α-LA enriched permeate 429 includes the majority of the α-LA proteins from the alkaline whey protein mixture, but also includes a significant amount of residual ß-LG and cGMP. The amounts of the ß-LG and cGMP are further reduced by performing a cold-incubation enzymatic hydrolysis on the permeate 429 in step 434. The cold-incubation includes reducing or maintaining the temperature of the permeate 429 below room temperature (e.g., less than 10° C., between 7-10° C., etc.) while adding protease enzymes 436 that selectively hydrolyze the ß-LG and cGMP over the α-LA proteins. The enzymes may hydrolyze the proteins for 5 hours or less (e.g., 1 to 60 minutes), and the enzymatic hydrolysis may be stopped abruptly using, for example, flash heating.

The enzymatically hydrolyzed ß-LG and cGMP may be separated from the unhydrolyzed α-LA proteins in step 438. The separation may be done using ultrafiltration (UF) or a combination of ultrafiltration and diafiltration (UF/DF). The filtration process separates the hydrolyzed permeate into (i) an α-LA-enriched retentate 440 that includes unhydrolyzed α-LA proteins and (ii) an α-LA-depleted permeate 446 that includes the hydrolysate products of the ß-LG and cGMP. The majority of the proteins in the α-LA-enriched retentate 440 are α-LA proteins, where the weight ratio of α-LA proteins to ß-LG proteins (α/ß) is 5:1 or more (e.g., 6:1 or more, 7:1 or more, 8:1 or more, 9:1 or more, 10:1 or more, 15:1 or more, 20:1 or more, 5:1 to 10:1, 5:1 to 20:1, etc.). The hydrolysis of the cGMP in the permeate 429 significantly reduces their presence in the α-LA-enriched retentate 440. cGMP amounts may be 3 wt. % or less, 2 wt. % or less, 1 wt. % or less, by dry weight in the retentate 440.

The α-LA-enriched retentate 440 may undergo spray drying in step 442 to remove residual water and form a powder of the high-purity α-LA product 444. The spray drying may form a powdered high-purity α-LA product 444. The high-purity α-LA product 444 may be used in a variety of applications such as infant formula (including hypoallergenic infant formula that requires very low levels of ß-LG and cGMP to accompany the α-LA proteins), sports nutrition products, and relaxation and/or mood altering products.

The α-LA-depleted permeate 446 that includes the majority of the ß-LG and cGMP hydrolysis products may be concentrated in step 448. The concentration methods may include evaporation of a portion of the water from the permeate 446 by heating and/or the application of vacuum. The concentrated permeate may undergo spray drying at step 450 to form a powder of the hydrolyzed proteins, also referred to as the hydrolyzed whey permeate product 452. The hydrolyzed whey permeate product 452 has good water solubility characteristics, and finds uses as a protein hydrolysate additive in foods and beverages. For example, the hydrolyzed whey permeate product 452 may be used in clear beverages, enteral nutrition products, soft drinks, coffees, sports nutrition products, and confectionary foods, among other kinds of foods and beverages.

Exemplary Systems for Making High-Purity α-LA Compositions

Figure 5:
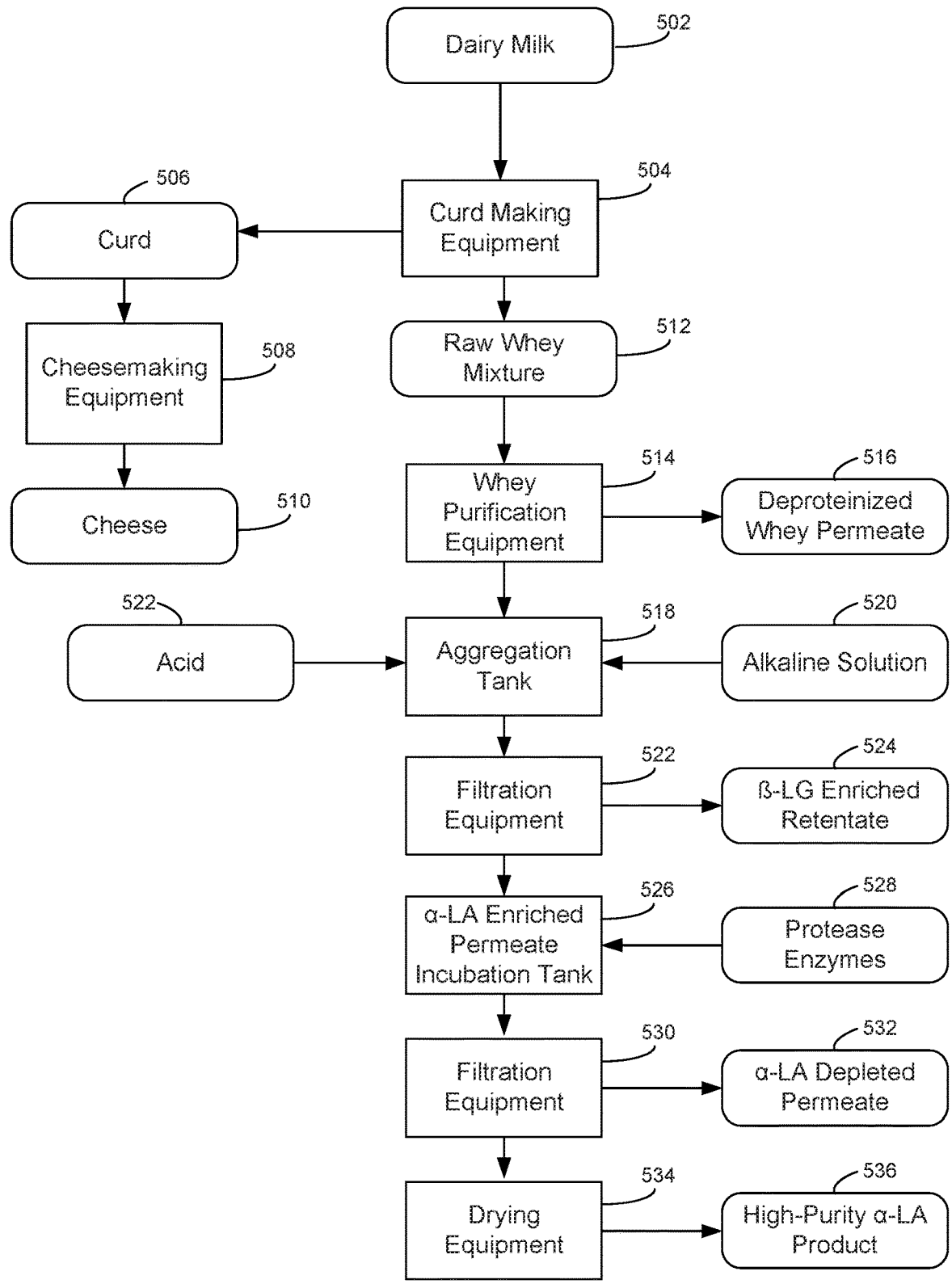
FIG. 5 shows selected components in a system for making a high-purity α-lactalbumin compositions according to embodiments of the invention.

FIG. 5 shows a simplified schematic for a system 500 to make high-purity α-LA products. The system 500 includes curd making equipment 504 that can take dairy milk 502 and convert it into curds 506 and a raw whey mixture 512. In some embodiments, the curd making equipment 504 includes a vat or pipeline in which the dairy milk 502 is formed into a curd coagulum through the use of added acids and/or enzymes. The curd coagulum is then cut to permit the separation of the curds 506 from the raw whey mixture 512. In other embodiments, the curd making equipment 504 includes a conduit through which the milk 502 flows and coagulates into curd particulates mixed together with the liquid whey. The curd making equipment also includes separation sub-systems that separate the particles of curd 506 from the raw whey mixture 512.

The curds 506 may be sent to cheesemaking equipment 508 where they are converted into cheese 510. When the cheese 510 produced is pasta filata cheese, the cheesemaking equipment 508 may include mixers and augers that convert the cheese curd 506 into a heated, kneaded and stretched mass of pasta filata cheese. The equipment 508 may also include cooling and shaping equipment that cools and shapes the pasta filata cheese into a form (e.g., block, ribbon, sheet, rod, etc.) that can be cut into smaller shapes such as shreds, slices, sticks, and cubes, among other shapes. For additional details on systems used to make pasta filata cheeses, please see co-assigned U.S. Pat. No. 7,585,537 to Merrill et al, titled "Cheese and Methods of Making Such Cheese" the entire contents of which are herein incorporated by reference for all purposes.

The raw whey mixture 512 may be sent to whey separation/clarification/filtration equipment 514 that removes fat and particulates in the mixture, as well as filters the larger proteins in the whey from smaller sugars and minerals. The filtration equipment may include one or more ultrafiltration membranes that separate the proteins in the mixture 512 from smaller molecules like sugars, minerals and water that become the deproteinized whey permeate 516.

The concentrated whey proteins (e.g., WPC 80), which also include cGMP, may be sent to an aggregation tank 518, where they are diluted with water to reduce the total solids and/or protein content to a predetermined level (e.g., 9% to 12% total solids, 7.2% to 9.6% protein, etc). An alkaline solution 520 may be added to the diluted whey protein mixture in the tank 518 to raise the pH of the mixture above neutral (i.e., 7). Exemplary pHs for the alkaline whey protein mixture may be 7.5 or more, 8 or more, 9 or more, 10 or more, between 9 and 11, etc. The alkaline whey protein mixture may also be cooled to a temperature of 10° C. or less (e.g. about 7° C. to about 10° C.) and agitated to facilitate the aggregation of the ß-LG proteins in the mixture. Following the aggregation of the ß-LG proteins, an acid 522 may be added to the aggregated whey protein mixture in the aggregation tank 518 to adjust the pH closer to neutral or acidic.

The aggregated whey protein mixture may be sent to filtration equipment 522 that separates the ß-LG aggregates from a α-LA enriched permeate. The filtration equipment 522 may include ultrafiltration equipment that includes one or more filtration membranes that holds the aggregated ß-LG proteins in the retentate while passing the un-aggregated ß-LG and α-LA proteins as well as the cGMP to the permeate. The UF equipment may include a spiral-wound, ceramic, and/or flat-sheet membrane module for cross-flow filtration of the aggregated whey protein mixture. The membrane module may include (i) a perforated center conduit through which a permeate can infiltrate and travel, and (ii) one or more sheets wrapped around the center conduit, or (iii) stacked flat-sheets. At least one of the sheets is an ultrafiltration membrane that blocks the migration of the retentate while permitting the radial transfer of the liquid permeate to and through the center conduit. The ultrafiltration member sheet may be made from an organic polymer or inorganic material. Examples of suitable organic polymers include one or more of cellulose acetate, polysulfone, polyvinylidene fluoride, polyethersulfone, polyesters, and polyamide, among other types of organic polymers. Examples of suitable inorganic materials may include mineral and/or ceramic based membranes.

The ultrafiltration membrane has a molecular weight cutoff (MWCO) that blocks the passage of the aggregated ß-LG proteins while permitting the transfer of the non-aggregated α-LA and cGMP through the membrane. The MWCOs may be set for a multiple of the 18.4 kDa molecular weight of an ß-LG protein (e.g., 36.8 kDa or more (×2), 55.2 kDa or more (×3), 73.6 kDa or more (×4), 92 kDa or more (×5), etc.). Exemplary MWCOs may range from 40 kDa to 500 kDa, depending on the extent of ß-LG protein aggregation in the aggregated whey protein mixture. The UF equipment may also be configured to permit diafiltration (DF) by introducing water to the UF membrane during and/or after the introduction of the aggregated whey protein mixture to further separate the ß-LG-enriched retentate 524 from the α-LA-enriched permeate. The ß-LG-enriched retentate 524 may be dried and formed into ß-LG-enriched product.

Alternate examples of the filtration equipment 522 may include UF designs for dead-end filtration, where the aggregated whey protein mixture meets a membrane barrier that holds particles larger than the membrane pore size back as the ß-LG-enriched retentate 524 while permitting smaller particles and liquid through as the α-LA enriched permeate. The UF membrane barrier may have a plate-and-frame design that holds the membrane itself as a flat sheet that intersects the flow of the alkaline whey protein mixture. In some examples, the membrane barrier is made of an organic polymer such as cellulose acetate, polysulfone, polyvinylidene fluoride, polyethersulfone, polyesters, and polyamide, among other types of organic polymers. In additional examples, the membranes are made from inorganic materials such as mineral and/or ceramic materials. Exemplary MWCOs include a range from 40 to 500 kDa (e.g., 50 to 100 kDa), depending upon the extent of aggregation in the ß-LG proteins.

The α-LA enriched permeate containing the majority of the α-LA proteins is sent to an α-LA enriched permeate incubation tank 526. The incubation tank 526 may include a refrigeration sub-system that cools the α-LA enriched permeate to a temperature of 10° C. or less before adding protease enzymes 528 to the tank. The protease enzymes 528 initiate a selective enzymatic hydrolysis of the remaining ß-LG and cGMP over the α-LA proteins. The incubation tank 526 may also include or be coupled to heating equipment that can initiate a rapid increase in the temperature of the hydrolyzing proteins to flash terminate the activity of the protease enzyme(s).

The enzymatically hydrolyzed α-LA enriched permeate is sent to filtration equipment 430 where the larger, unhydrolyzed α-LA proteins are filtered as the retentate from an α-LA-depleted permeate 532 that includes the ß-LG and cGMP hydrolysates. Exemplary filtration equipment 530 may include cross-flow ultrafiltration equipment such as a spiral-wound, ceramic, or flat-sheet membrane module. The spiral-wound membrane module may include (i) a perforated center conduit through which a permeate can infiltrate and travel, and (ii) one or more sheets wrapped around the center conduit. At least one of the sheets is an ultrafiltration membrane that blocks the migration of the retentate while permitting the radial transfer of the liquid permeate to and through the center conduit. The ultrafiltration membrane sheet may be made from an organic polymer. Examples of suitable organic polymers include one or more of cellulose acetate, polysulfone, polyvinylidene fluoride, polyethersulfone, polyesters, and polyamide, among other types of organic polymers. The membranes may also be made from inorganic materials such as mineral and/or ceramic materials.

The ultrafiltration equipment includes an ultrafiltration membrane having a MWCO that holds the unhydrolyzed α-LA proteins while passing the majority or all of the ß-LG and cGMP hydrolysates into the permeate. Exemplary MWCO ranges include 5-15 kDa, 8-14 kDa, etc. The ultrafiltration equipment may also be configured to permit diafiltration in addition to ultrafiltration of the enzymatically hydrolyzed ß-LG depleted permeate.

The α-LA-enriched retentate may be sent to drying equipment 534 that can convert the retentate into a powdered high-purity α-LA product 536. The drying equipment 534 may include a spray drier having a spray nozzle that can atomize the wet α-LA-enriched retentate and have it make contact with a drying gas that flows co-directionally or counter-directionally to the atomized retentate. The drying gas is normally heated, and may have a temperature ranging from 20-220° C. when contacting the atomized retentate. Examples of the drying gas include filtered air and nitrogen (e.g., nitrogen with a purity of 90 mol. % or more, 95 mol. % or more, 99 mol. % or more, etc.). The spray-dried, high-purity α-LA product typically has particle sizes ranging from 10 to 500 µm (e.g., 100-300 µm).

Figure 6:
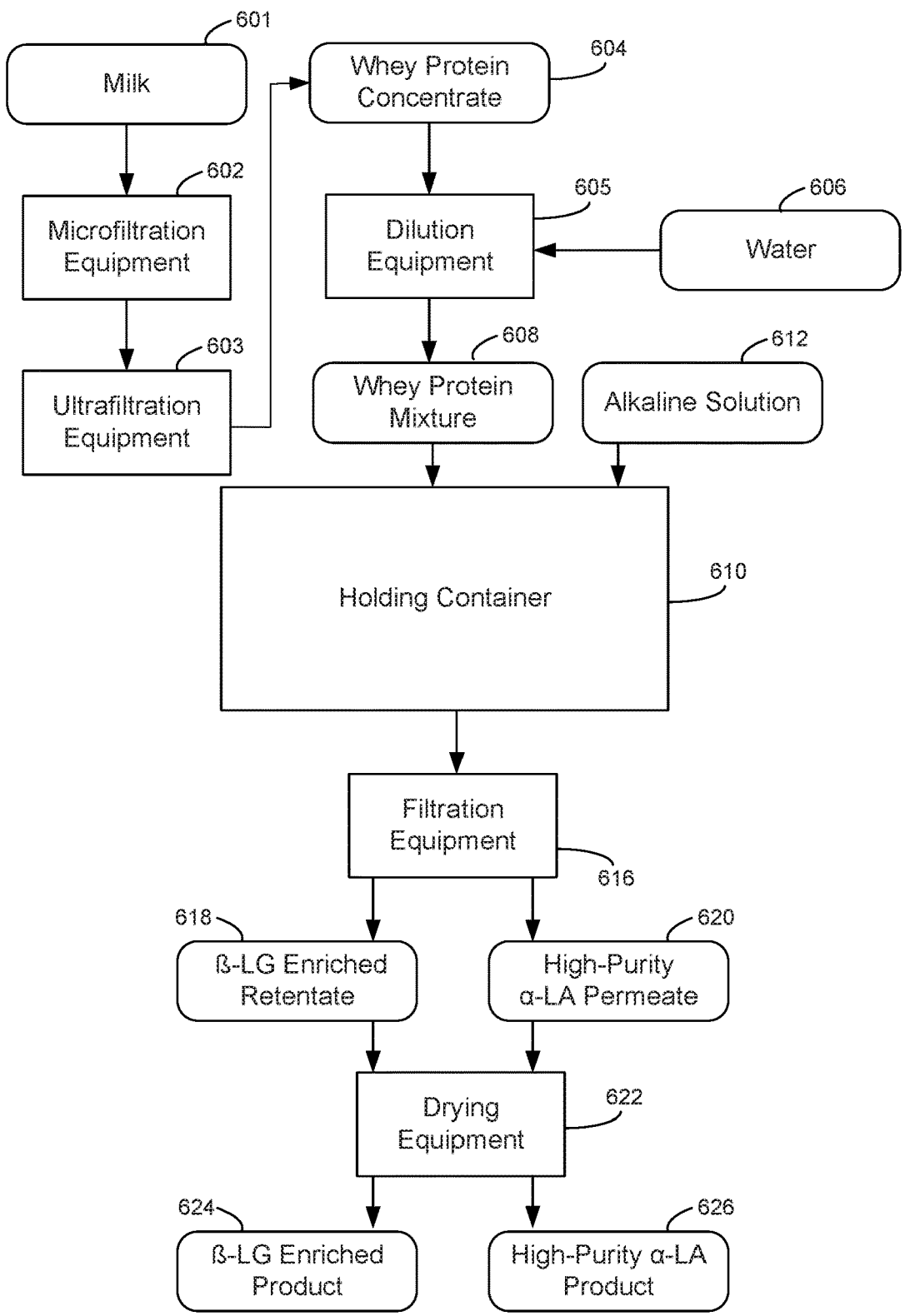
FIG. 6 shows selected components in another system for making a high-purity α-lactalbumin and ß-lactoglobulin enriched compositions from milk according to embodiments of the invention.

FIG. 6 shows another simplified schematic of selected components of a system 600 for making ß-LG-enriched and high-purity α-LA products from native whey protein according to embodiments of the invention. The system 600 includes microfiltration equipment 602 and ultrafiltration equipment 603 that converts starting milk 601 into a native whey protein concentrate or isolate 604. The native whey protein concentrate or isolate 604 may be supplied to dilution equipment 605 that is used to dilute a native whey protein concentrate or isolate 604 with water 606 to a pre-defined level of total proteins (e.g., 7.2-9.6 wt. % total protein). The diluted native whey protein mixture 608 is then sent to a holding container 610, which includes sub-systems to cool the mixture below room temperature (e.g., 7° C. to 10° C.) and provide an alkaline solution 612 to increase the pH of the mixture to an alkaline level (e.g., pH greater than 7.5, greater than 8, greater than 9, greater than 10, between 10 and 11, etc.). The holding container 610 may also include a sub-system to mix or agitate the mixture during the ß-LG aggregation period.

The aggregated whey protein mixture may then be sent to filtration equipment 616 to separate the aggregated ß-LG retentate 618 from the α-LA enriched permeate. The ß-LG retentate 618 may be separately sent from the filtration equipment 616 to drying equipment 622 that dries the retentate 618 into a ß-LG-enriched product 624 and high-purity α-LA product 626.

EXAMPLES

Example 1—Production of α-Lactalbumin Enriched Composition

An α-LA enriched composition is made from whey protein concentrate (WPC) that is a by-product of cheese making. The process starts with WPC retentate (80% protein on dry basis) that is concentrated using ultrafiltration (UF) of the raw whey mixture separated from cheese curd. The 80% WPC is transferred to a temperature-controlled holding tank where it is mixed with water to make a 10.3% total solids concentration by wt., diluted whey protein solution. The holding tank can hold a 1,000 lbs batch of the whey protein mixture, where 103 lbs of the 80% WPC solids are mixed with water to form the diluted whey protein solution.

The diluted whey protein solution is then made alkaline by adding 10% potassium hydroxide (KOH) to the holding tank under agitation. For the 1,000 lbs batch, 22 lbs of 10% KOH is used to raise the pH of the whey mixture to 10.45. The alkaline whey protein solution was held at about 7.2° C. or less with agitation, for 5 hours.

Following cold incubation, 10% citric acid is added to the alkaline whey protein solution to lower the pH to 7. After neutralization, the protein mixture is subjected to first ultrafiltration with a MWCO 100 kDa filter that separates the aqueous permeate from the retentate. The first α-LA enriched permeate, which comprises α-lactalbumin, glycomacropeptides, and residual β-lactoglobulin, is concentrated before spray drying to produce an α-LA enriched product. The first retentate, comprises β-lactoglobulin aggregates, is also spray dried to produce a powdered β-lactoglobulin product.

The ratio of α-lactalbumin to β-lactoglobulin of the starting material 80% WPC retentate and the finished product α-lactalbumin enriched powder is determined by a capillary electrophoresis method. The results listed in Table 1 show a dramatic inversion in the relative concentrations of α-LA and ß-LG between the 80% WPC retentate and the α-LA-enriched product:

TABLE 1

α/β Ratio in Starting WPC Retentate and α-LA Enriched Product

| Sample Description | α/β Ratio |
|---|---|
| 80% WPC Retentate | 0.39 |
| α-Lactalbumin Enriched Whey Protein Composition | 5.40 |

Example 2—Production of High Purity α-Lactalbumin Composition

A high purity α-LA composition is made from whey protein concentrate (WPC) that is a by-product of cheese making. The process starts with WPC retentate (80% protein on dry basis) that is concentrated using ultrafiltration (UF) of the raw whey mixture separated from cheese curd. The 80% WPC is transferred to a temperature controlled holding tank where it is mixed with water to make a 10.3% total solids concentration, by wt., diluted whey protein solution. The holding tank can hold a 1,000 lbs batch of the whey protein mixture, where 103 lbs of the 80% WPC solids are mixed with water to form the diluted whey protein solution.

The diluted whey protein solution is then made alkaline by adding 10% potassium hydroxide (KOH) to the holding tank under agitation. For the 1,000 lbs batch, 22 lbs of 10% KOH is used to raise the pH of the whey mixture to 10.45. The alkaline whey protein solution was held at about 7.2° C. or less with agitation, for 5 hours.

Following cold incubation, 10% citric acid is added to the alkaline whey protein solution to lower the pH to 7. After neutralization, the protein mixture is subjected to first ultrafiltration with a MWCO 100 kDa filter that separates the aqueous permeate from the retentate. The first α-LA enriched permeate comprises of α-lactalbumin, glycomacropeptides, and residual β-lactoglobulin. The first retentate comprises of β-lactoglobulin aggregates which is then spray dried to produce a powdered β-lactoglobulin product.

The first α-LA enriched permeate is treated with protease enzyme while remaining cold. Addition of the protease enzyme(s) starts the phase of the protein hydrolysis that selectively hydrolyzes at least a portion of glycomacropeptides and residual β-lactoglobulin in the first permeate fraction. In this example, the protease enzyme is a neutral protease sourced from *Bacillus subtilis* and sold commercially under the tradename Protamex® by Novozymes of Denmark. It is added to the first permeate at a level of about 0.6% by wt. of the total protein in the substrate followed by incubation for at least 1 hr. Thereafter the enzymes are inactivated by heating the mixture to 90.5° C. for 10 minutes.

Following inactivation, the enzymatically treated first α-LA enriched permeate is subjected to a second ultrafiltration with a MWCO 10 kDa filter to separate hydrolyzed glycomacropeptide/β-lactoglobulin fragments as second permeate and high purity α-lactalbumin as second retentate. The second retentate is then spray dried to produce a powdered high purity α-lactalbumin whey protein composition, whereas the second permeate is concentrated before spray drying into hydrolyzed whey protein powder composition.

The ratio of α-lactalbumin to β-lactoglobulin of the starting material 80% WPC retentate and the finished product high purity α-lactalbumin powder is determined by capillary electrophoresis method. The results listed in Table 2 show an even more dramatic inversion in the relative concentrations of α-LA and ß-LG between the 80% WPC retentate and the high-purity α-LA product when an optional enzymatic hydrolysis step is introduced:

TABLE 2

α/β Ratio in Starting WPC Retentate
and High Purity α-LA Product

| Sample Description | α/β Ratio |
| --- | --- |
| 80% WPC Retentate | 0.39 |
| High Purity α-Lactalbumin Whey Protein Composition | 25.50 |

Amino acid profiles of the starting material 80% WPC retentate and the finished product high purity α-LA powder are summarized in Table 3. A substantial increase in both Cystine (from 2.289 to 3.716 g AA/100 g protein) and Tryptophan (from 1.784 to 4.029 g AA/100 g protein) is observed in the high purity α-LA product, making it more suitable for use as an infant formula ingredient compared to the regular WPC 80 powder dried from 80% WPC retentate directly.

TABLE 3

Amino Acid Profile of Starting WPC Retentate
and High Purity α-LA Product

| Amino Acid | 80% WPC Retentate (g AA/100 g Protein) | High Purity α-Lactalbumin Whey Protein Composition (g AA/100 g Protein) |
| --- | --- | --- |
| Alanine | 4.529 | 2.517 |
| Arginine | 2.531 | 1.224 |
| Aspartic acid | 10.651 | 14.036 |
| Cystine | 2.289 | 3.716 |
| Glutamic acid | 17.284 | 16.511 |
| Glycine | 1.607 | 2.115 |
| Histidine | 1.825 | 2.294 |
| Isoleucine | 6.365 | 6.739 |
| Leucine | 9.931 | 8.698 |
| Lysine | 9.122 | 8.824 |
| Methionine | 2.091 | 0.873 |
| Phenylalanine | 3.173 | 3.418 |
| Proline | 6.058 | 4.385 |
| Serine | 4.906 | 4.988 |
| Threonine | 7.331 | 6.885 |
| Tryptophan | 1.784 | 4.029 |
| Tyrosine | 2.986 | 3.400 |
| Valine | 5.536 | 5.348 |

Example 3—Production of High Purity α-Lactalbumin Composition from Native Whey

Example 3 involves the production of a high purity α-LA composition made from native whey protein isolate (NWPI) derived from dairy source (raw milk, whole milk, or defatted milk) after microfiltration. The process starts with NWPI retentate (90% protein on dry basis) that is concentrated using ultrafiltration (UF) of the raw whey mixture separated from casein and fat using microfiltration. The 90% NWPI is transferred to a temperature controlled holding tank where it is mixed with water to make a 10.3% total solids concentration, by wt., diluted whey protein solution. The holding tank can hold a 1,000 lbs batch of the whey protein mixture, where 103 lbs of the 90% NWPI solids are mixed with water to form the diluted whey protein solution.

The diluted whey protein solution is then made alkaline by adding 10% potassium hydroxide (KOH) to the holding tank under agitation. For the 1,000 lbs batch, 17 lbs of 10% KOH is used to raise the pH of the whey mixture to 10.45. The alkaline whey protein solution was held at about 7.2° C. or less with agitation, for 5 hours.

Following cold incubation, 10% citric acid is added to the alkaline whey protein solution to lower the pH to 7. After neutralization, the protein mixture is subjected to first ultrafiltration with a MWCO 100 kDa filter that separates the aqueous permeate from the retentate. The first high purity α-LA permeate comprises of α-lactalbumin and residual β-lactoglobulin and spray dried to produce a powdered high purity α-LA product. The first retentate comprises of β-lactoglobulin aggregates which is then spray dried to produce a powdered β-lactoglobulin product.

The ratio of α-lactalbumin to β-lactoglobulin of the starting material 90% NWPI retentate and the finished product high purity α-lactalbumin powder is determined by capillary electrophoresis method. The results are shown in Table 4:

TABLE 4

α/β Ratio in Starting NWPI Retentate
and High Purity α-LA Product

| Sample Description | α/β Ratio |
| --- | --- |
| 90% NWPI Retentate | 0.41 |
| High Purity α-Lactalbumin Native Whey Protein Composition | 5.10 |

Amino acid profiles of the starting material NWPI retentate and the finished product high purity α-LA powder are summarized in Table 5. A significant increase in both Cystine (from 2.857 to 3.181 g AA/100 g protein) and Tryptophan (from 2.038 to 3.660 g AA/100 g protein) in conjunction with inherently low Threonine (4.759) compared to regular WPC80 (7.331) are observed in the high purity α-LA product, making it even more suitable for use as an infant formula ingredient.

TABLE 5

Amino Acid Profile of Starting NWPI Retentate
and High Purity α-LA Product

| Amino Acid | 90% NWPI Retentate (g AA/100 g Protein) | High Purity α-Lactalbumin Native Whey Protein Composition (g AA/100 g Protein) |
| --- | --- | --- |
| Alanine | 4.422 | 3.354 |
| Arginine | 2.789 | 2.221 |
| Aspartic acid | 10.688 | 12.485 |

TABLE 5-continued

Amino Acid Profile of Starting NWPI Retentate and High Purity α-LA Product

| Amino Acid | 90% NWPI Retentate | High Purity α-Lactalbumin Native Whey Protein Composition |
|---|---|---|
| | (g AA/100 g Protein) | |
| Cystine | 2.857 | 3.181 |
| Glutamic acid | 17.098 | 16.152 |
| Glycine | 1.567 | 1.842 |
| Histidine | 2.029 | 2.347 |
| Isoleucine | 5.566 | 5.699 |
| Leucine | 12.314 | 11.285 |
| Lysine | 10.187 | 10.220 |
| Methionine | 2.433 | 1.753 |
| Phenylalanine | 3.711 | 3.943 |
| Proline | 5.016 | 4.162 |
| Serine | 3.560 | 4.063 |
| Threonine | 4.630 | 4.759 |
| Tryptophan | 2.038 | 3.660 |
| Tyrosine | 3.682 | 3.876 |
| Valine | 5.412 | 4.998 |

Example 4—Production of High Purity α-Lactalbumin Composition from Native Whey Powder Example 4 involves the production of a high purity α-LA composition made from native whey protein isolate powder (NWPI powder) derived from the above NWPI retentate (90% protein on dry basis) after spray drying. The process starts with reconstitution of the NWPI powder with water into 10.3% total solids concentration, by wt., whey protein solution (90% NWPI). The 90% NWPI is then transferred to a temperature-controlled holding tank. The holding tank can hold a 1,000 lbs batch of the whey protein solution, where 103 lbs of the 90% NWPI solids are mixed with water.

The whey protein solution is then made alkaline by adding 10% potassium hydroxide (KOH) to the holding tank under agitation. For the 1,000 lbs batch, 17 lbs of 10% KOH is used to raise the pH of the whey mixture to 10.45. The alkaline whey protein solution was held at about 7.2° C. or less with agitation, for 5 hours.

Following cold incubation, 10% citric acid is added to the alkaline whey protein solution to lower the pH to 7. After neutralization, the protein mixture is subjected to first ultrafiltration with a MWCO 100 kDa filter that separates the aqueous permeate from the retentate. The first high purity α-LA permeate comprises of α-lactalbumin and residual β-lactoglobulin and spray dried to produce a powdered high purity α-LA product. The first retentate comprises of β-lactoglobulin aggregates which is then spray dried to produce a powdered β-lactoglobulin product.

The ratio of α-lactalbumin to β-lactoglobulin of the starting material NWPI powder and the finished product high purity α-lactalbumin powder is determined by capillary electrophoresis method. The results are shown in Table 6:

TABLE 6

α/β Ratio in Starting NWPI Powder and High Purity α-LA Product

| Sample Description | α/β Ratio |
|---|---|
| NWPI Powder | 0.48 |
| High Purity α-Lactalbumin Native Whey Protein Composition | 10.10 |

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the enzyme" includes reference to one or more enzymes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of making a powdered dairy composition, the method comprising:
   providing a whey protein mixture;
   adding an alkaline solution to the whey protein mixture to make an alkaline whey protein mixture, wherein a portion of ß-lactoglobulin in the alkaline whey protein mixture forms ß-LG aggregates, further wherein the alkaline whey protein mixture lacks a protease enzyme that selectively hydrolyzes the ß-lactoglobulin, and wherein the alkaline whey protein mixture has a temperature of 10° C. or less during the aggregation of the ß-LG aggregates;
   filtering the alkaline whey protein mixture into (i) a ß-LG aggregate composition and (ii) an α-LA enriched composition; and
   drying a final α-lactalbumin enriched composition sourced from the α-LA enriched composition into the powdered dairy composition, wherein the powdered dairy composition comprises at least 70 wt. % α-lactalbumin on a protein basis.

2. The method of claim 1, wherein the α-LA enriched composition further comprises glycomacropeptides.

3. The method of claim 1, wherein the whey protein mixture is derived from a dairy source selected from the group consisting of raw milk, skim milk, and partially defatted milk.

4. The method of claim 1, wherein the whey protein mixture is a native whey protein mixture made by microfiltration of a starting milk.

5. The method of claim 1, wherein the whey protein mixture is derived from a cheesemaking process that involves separating whey from curd and filtering the whey to form the whey protein mixture and a deproteinized permeate.

6. The method of claim 1, wherein the whey protein mixture is formed by diluting whey protein concentrate or whey protein isolate with water.

7. The method of claim 1, wherein the whey protein mixture comprises 5 wt. % to 15 wt. % whey protein concentration.

8. The method of claim 1, wherein the alkaline solution comprises sodium hydroxide, potassium hydroxide, calcium hydroxide, ammonium hydroxide, or combinations thereof.

9. The method of claim 1, wherein the alkaline whey protein mixture has a pH of 10 or more.

10. The method of claim 1, wherein the method further comprises lowering a temperature of the whey protein mixture to 10° C. or less before adding the alkaline solution.

11. The method of claim 1, wherein the alkaline whey mixture is agitated for 1 minute to 12 hours during the aggregation of the ß-LG aggregates.

12. The method of claim 1, wherein the alkaline whey protein mixture is filtered with an ultrafiltration membrane having a molecular weight cut-off of 40 kDa to 500 kDa.

13. The method of claim 12, wherein the ultrafiltration membrane is a spiral-wound polymeric membrane, a plate and frame membrane, or a ceramic membrane module.

14. The method of claim 1, wherein the method further comprises adding a protease enzyme to the α-LA enriched composition to form an enzymatically treated α-LA enriched composition, wherein the protease enzyme hydrolyzes at least a portion of residual ß-lactoglobulin in the enzymatically treated α-LA enriched composition.

15. The method of claim 14, wherein the α-LA enriched composition further comprises glycomacropeptides, and the protease enzyme hydrolyzes at least a portion of the glycomacropeptides.

16. The method of claim 14, wherein the method further comprises filtering the enzymatically treated α-LA enriched composition into the final α-lactalbumin enriched composition, and a permeate comprising at least a portion of the enzymatically hydrolyzed residual ß-lactoglobulin.

17. The method of claim 14, wherein the permeate further comprises enzymatically hydrolyzed glycomacropeptides.

18. The method of claim 14, wherein the protease enzyme comprises an acid protease enzyme, neutral protease enzyme, or alkaline protease enzyme.

19. The method of claim 14, wherein the method further comprises flash heating the first permeate to stop hydrolysis activity of the protease enzyme.

20. The method of claim 1, wherein the drying of the final α-lactalbumin enriched composition comprises spray drying.

21. The method of claim 1, wherein the powdered dairy composition is at least 80 wt. % whey proteins on a dry basis.

22. The method of claim 1, wherein the powdered dairy composition has a weight ratio of α-lactalbumin to ß-lactoglobulin greater than 5:1.

23. The method of claim 1, wherein the powdered dairy composition has less than 1 wt. % glycomacropeptides on a dry basis.

24. A high-purity α-lactalbumin dairy composition comprising:
  80 dry wt. % or more whey proteins;
  5:1 or more weight ratio of α-lactalbumin to ß-lactoglobulin;
  1 dry wt. % or less glycomacropeptides; and
  one or more enzyme hydrolysates of ß-lactoglobulin, wherein the one or more enzyme hydrolysates of ß-lactoglobulin have a molecular weight of 5-15 kDa.

25. The high-purity α-lactalbumin dairy composition of claim 24, wherein the composition is a powder.

26. The high-purity a-lactalbumin dairy composition of claim 24, wherein the weight ratio of α-lactalbumin to ß-lactoglobulin is 10:1 or more.

27. The high-purity α-lactalbumin dairy composition of claim 24, wherein the composition has 30 dry wt. % or more α-lactalbumin.

28. The high-purity α-lactalbumin dairy composition of claim 24, wherein the composition has 10 dry wt. % or less ß-lactoglobulin.

* * * * *